United States Patent [19]

Espinosa

[11] Plant 5,237

[45] May 29, 1984

[54] *PHOTINIA×FRASERI* CV. MONSTOCK

[75] Inventor: Gavin Espinosa, Azusa, Calif.

[73] Assignee: Monrovia Nursery Co., Azusa, Calif.

[21] Appl. No.: 402,059

[22] Filed: Jul. 26, 1982

[51] Int. Cl.[3] ..... A01H 5/00

[52] U.S. Cl. ..... Plt./54

[58] Field of Search ..... Plt./54

*Primary Examiner*—James R. Feyrer

[57] ABSTRACT

A new and distinct sport of *Photinia×fraseri* Dress shrub (popularly known as Photinia) which hereinafter will be referred to as *Photinia×fraseri* cultivar Monstock. Differing from its parent, *Photinia×fraseri* by the new selection, *Photinia×fraseri* cv. Monstock possessing a unique combination of smaller leaves with undulate margins and finer serrations along with reddish coppery juvenile foliage and stipules which are green and persistent contrasting with the stems which are a pale red color. Another unique character of *Photinia×fraseri* cv. Monstock is its compact growth habit.

3 Drawing Figures

DISCOVERY

This invention relates to a new and distinct selection of *Photinia×fraseri,* a member of the rose family, Rosaceae. The parent, *Photinia×fraseri* is a hybrid of known parentage, *P.glabra×Photinia serrulata. Photinia×fraseri* cv. Monstock was discovered as a vegetative sport from a branch of *Photinia×fraseri* at Monrovia Nursery Company, 18331 East Foothill Boulevard, Azusa, Calif. in June of 1977.

The plant to date is known to exist only within the boundaries of Monrovia Nursery and has not been offered for sale or described in any publication.

REPRODUCTION

This new selection has been strictly asexually reproduced by cuttings at Monrovia Nursery Company. The unique characteristics that set *Photinia×fraseri* cv. Monstock apart from the parent plant have a potential to be lost by sexual reproduction, therefore seed propagation is prohibited and propagation is retricted to asexual reproduction. Seed progeny from this new selection has not been observed.

BRIEF DESCRIPTION OF THE DRAWING

FIG. 1 photograph exhibits the size and growth habit of the parent plant on the left and my selection on the right. This photo compares the open and more loose habit of the parent to the tighter more compact habit of my selection. Comparison of the new growth, bright red on the parent and orange coppery on the selection should also be noted.

FIG. 2 photograph exhibits comparisons of the parent on the left and my selection on the right of their foliage size, shape of leaves, and margin undulations.

CHARACTERISTICS

*Photinia×fraseri* cv. Monstock differs from its parent plant *Photinia×fraseri* (see accompanying photograph #1) in its distinctive compact dense growth habit and smaller orange coppery new foliage separating it from its parent which has a loose open habit and larger scarlet red new foliage.

Photograph #2 exhibits close ups of the leaves. The leaves are approximately half the size in *Photinia×fraseri* cv. Monstock along with its green petiole, undulate and finely serrated leaf margins and green persistent stipules contrasting against the pale red stems. The parent, *Photinia×fraseri* having larger leaves, red petioles, larger serrations and margins not undulate and only a few persistent stipules which do not contrast, as the stem is the same color.

The new *Photinia×fraseri* cv. Monstock was deliberately selected for these qualities listed above and shown in the accompanying photographs.

DESCRIPTION

Below is a detailed description of *Photinia×fraseri* cv. Monstock, all color terminology is from the British Horticultural Color Charts.

Overall size and habit: After five years my selection has a height of approximately four feet and a spread of five feet, whereas, the parent would be approximately 8 to 10 feet in height with a 8 foot spread. The ultimate height of my selection I believe to be approximately 5 feet with a width of 6 ft. *Photinia×fraseri* exhibits a strong upward branching habit. My selection does exhibit a slight upward branching habit however the overall habit is a more compact and dense shrub. Whereas the parent exhibits a more loose and open habit as compared in FIG. 1.

FOLIAGE

Size: Leaf tip to base, excluding petiole is $1\frac{1}{4}''$ to $2\frac{1}{4}''$ in length, $\frac{3}{4}''$ to $1\frac{1}{2}''$ width. Parent plant foliage 3–4″ in length; $1\frac{5}{8}''$–2″ in width.

Shape: Obovate elliptic. The tip cuspidate to acuminate, the base attevate.

Color:

*Juvenile.*—New growth variable from Maroon 1030, Chrysanthemum Crimson 824 and Oxblood Red 00823/2 on the upper and lower leaf surface.

*Mature.*—Upper surface glossy Spinach Green 0960 and lower surface Fern Green 0862/1.

Margins: Undulate and serrulate with serrations closer together nearing the tip.

Texture: Coriaceous.

Arrangement: Alternate with short internodes.

Pubescense: Both surfaces completely glabrous.

Petiole: $\frac{1}{2}''$ to $\frac{5}{8}''$ in length with a few scattered hairs; color: Fern Green 0862/1.

Stipules: Persistent on current years growth.
Stem color: Current year — Current Red 821/1 mixed with Fern Green 0862/1.
Flower: Insignificant, creamy white.
Fruit: Not observed.
Petals: Approximately eight in number, $\frac{1}{8}'' \times \frac{1}{8}''$ in size, emarginate.
Stamens: Approximately 10 to 11 in number.
Style: Three.
Sepals: Seven.

Peduncle: $\frac{1}{4}''$ in length.

I claim:

1. A new and distinct *Photinia×fraseri* referred to as *Photinia×fraseri* cv. Monstock as substantially shown and described; a superior selection characterized by a densely compact habit; smaller foliage; persistent stipules on current growth; and its distinctive reddish coppery new foliage.

* * * * *

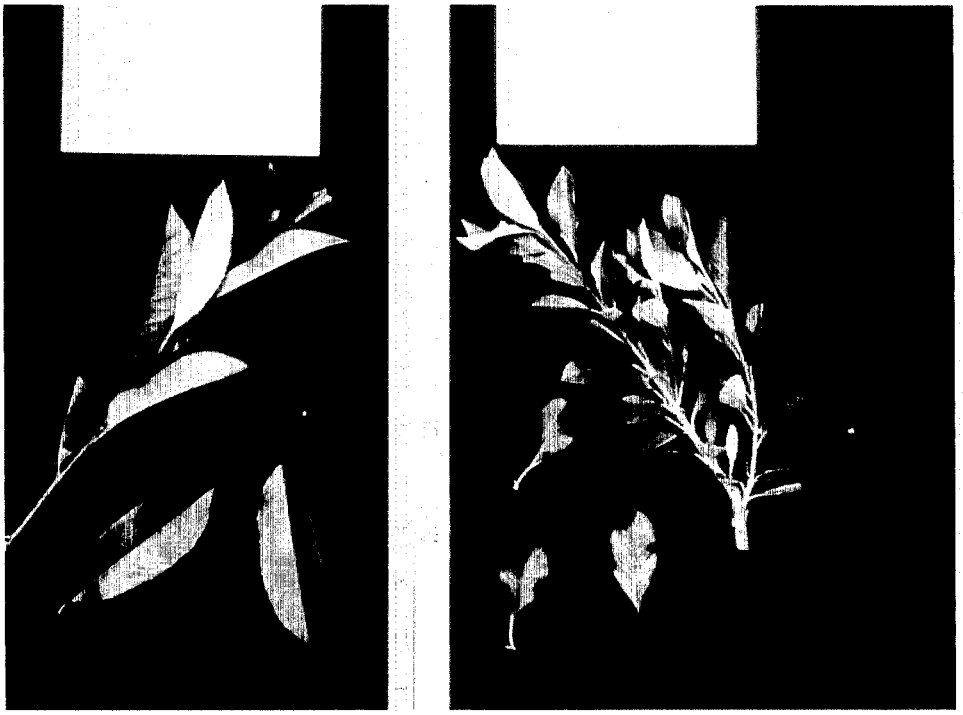
PARENT No.2 SELECTION
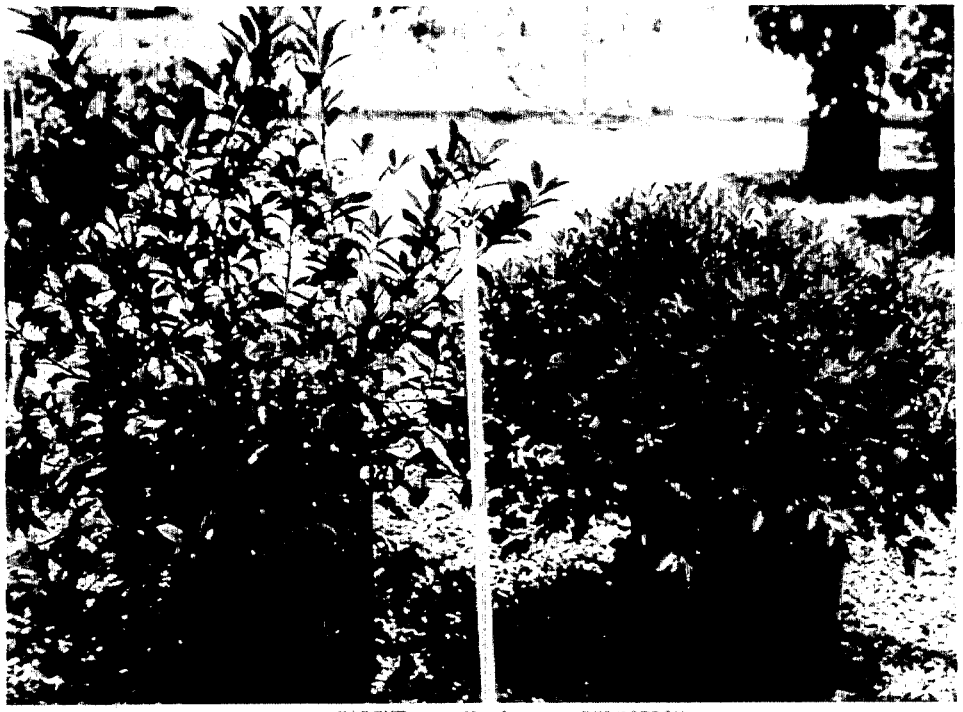
PARENT No.1 SELECTION